United States Patent
Lee et al.

(10) Patent No.: US 8,415,170 B2
(45) Date of Patent: Apr. 9, 2013

(54) METHOD FOR CONTINUOUSLY DETECTING GLUCOSE CONCENTRATION IN SAMPLE, KIT THEREOF AND METHOD FOR USING BIOSENSOR

(75) Inventors: Kun-Feng Lee, Kaohsiung County (TW); Chien-An Chen, Yonghe (TW); Hong-Wen Chang, Xinzhuang (TW); Yuh-Jiuan Lin, Taipei County (TW)

(73) Assignee: Industrial Technology Research Institute, Hsinchu County (TW)

( * ) Notice: Subject to any disclaimer, the term of this patent is extended or adjusted under 35 U.S.C. 154(b) by 504 days.

(21) Appl. No.: 12/717,542

(22) Filed: Mar. 4, 2010

(65) Prior Publication Data

US 2010/0304399 A1 Dec. 2, 2010

(30) Foreign Application Priority Data

May 26, 2009 (TW) .............................. 98117415 A

(51) Int. Cl.
*G01N 33/543* (2006.01)

(52) U.S. Cl.
USPC .......... 436/518; 422/400; 422/82.11; 435/14; 435/287.1; 435/288.7; 436/524; 436/525; 436/529; 436/164; 436/805; 436/808; 436/815; 436/827

(58) Field of Classification Search .................. None
See application file for complete search history.

(56) References Cited

U.S. PATENT DOCUMENTS

| | | | |
|---|---|---|---|
| 4,344,438 A * | 8/1982 | Schultz | 600/341 |
| 6,454,710 B1 * | 9/2002 | Ballerstadt et al. | 600/365 |
| 6,475,750 B1 | 11/2002 | Han et al. | |
| 2004/0106216 A1 | 6/2004 | Matsui et al. | |
| 2008/0193965 A1 | 8/2008 | Zeng | |
| 2009/0131773 A1 | 5/2009 | Struve et al. | |
| 2010/0049015 A1 * | 2/2010 | Martini et al. | 600/310 |

FOREIGN PATENT DOCUMENTS

TW 200806989 A 2/2008

OTHER PUBLICATIONS

Notification of examination opinion issued by the Taiwan Intellectual Property Office on Aug. 20, 2012, for the above-referenced application's counterpart application in Taiwan (Application No. 98117415).
Notification of examination opinion issued by the Taiwan Intellectual Property Office on Nov. 8, 2012, for the above-referenced application's counterpart application in Taiwan (Application No. 98117415).
Office Action (Notice of First examination opinion) issued by the China Intellectual Property Office on Oct. 26, 2012, for the above-referenced application's counterpart application in China (Application No. 200910151267.X).
Huang, "Introduction to Biosensor", Google, Mar. 26, 2009.

* cited by examiner

*Primary Examiner* — Chris L Chin
(74) *Attorney, Agent, or Firm* — Pai Patent & Trademark Law Firm; Chao-Chang David Pai

(57) ABSTRACT

The invention provides a method for continuously detecting glucose concentration in a sample, including: (a) providing a biosensor comprising a transducer and a polysaccharide covered on the surface of the transducer; (b) providing a carbohydrate binding protein solution, wherein the carbohydrate binding protein has at least one receptor, and the receptor is capable of binding to the polysaccharide and glucose; (c) mixing a sample and the carbohydrate binding protein solution to form a mixture; (d) contacting the mixture with the biosensor; (e) detecting the amount of carbohydrate binding proteins bound to the polysaccharide by the biosensor, wherein glucose concentration of the sample is inversely proportional to the amount of carbohydrate binding proteins bound to the polysaccharide; and (f) refreshing the surface of the biosensor with a high concentration glucose solution.

31 Claims, 6 Drawing Sheets

METHOD FOR CONTINUOUSLY DETECTING GLUCOSE CONCENTRATION IN SAMPLE, KIT THEREOF AND METHOD FOR USING BIOSENSOR

CROSS REFERENCE TO RELATED APPLICATIONS

This application claims priority of Taiwan Patent Application No. 98117415, filed on May 26, 2009, the entirety of which is incorporated by reference herein.

BACKGROUND OF THE INVENTION

1. Field of the Invention

The present invention relates to a method for detecting glucose, and in particular relates to a method for continuously detecting glucose concentration in a sample.

2. Description of the Related Art

The blood glucose is detected mainly through an enzyme reaction. However, the detection stability and accuracy do not satisfied the continuous glucose measuring requirement due to the gradual loss of enzyme activity and leaching of enzyme. The appearance of glucose binding protein and other specific receptors (chelates) provide a possible way to replace the enzyme detection method for a more stable continuous glucose detecting. One of the methods is the polysaccharide-lectin system. This system utilizes the competitive and aggregative properties of glucose, polysaccharide and lectin in the glucose detection, and it usually combined with fluorescence resonance energy transfer (FRET) for the detection. However, reverse binding of lectin and polysaccharide on a biosensor of the polysaccharide-lectin detection system has been shown to be deficient, wherein detection accuracy decreases over time. Therefore, the conventional polysaccharide-lectin system is not appropriate in the continuous blood glucose measuring.

BRIEF SUMMARY OF THE INVENTION

The invention provides a method for continuously detecting glucose concentration in a sample, comprising: (a) providing a biosensor comprising a transducer and a polysaccharide covered on the surface of the transducer; (b) providing a carbohydrate binding protein solution, wherein the carbohydrate binding protein has at least one receptor, and the receptor is capable of binding to the polysaccharide and glucose; (c) mixing a sample and the carbohydrate binding protein solution to form a mixture; (d) contacting the mixture with the biosensor; (e) detecting the amount of carbohydrate binding proteins bound to the polysaccharide by the biosensor, wherein glucose concentration of the sample is inversely proportional to the amount of carbohydrate binding proteins bound to the polysaccharide; and (f) refreshing the surface of the biosensor with a high concentration glucose solution.

The invention also provides a kit for continuously detecting glucose concentration in a sample, comprising: a biosensor comprising a transducer and a polysaccharide covered on the surface of the transducer; a reactive solution for reacting with the sample, wherein the reactive solution comprises a carbohydrate binding protein solution with a particular concentration; and a washing solution for refreshing the surface of the biosensor, wherein the washing solution comprises a high concentration glucose solution.

The invention further provides a method for using a biosensor, comprising: (a) providing a biosensor comprising a transducer and a polysaccharide covered on the surface of the transducer; (b) contacting a mixture of a reactive solution comprising a carbohydrate binding protein solution with a particular concentration and a sample with the biosensor, wherein the carbohydrate is capable of binding to the polysaccharide and glucose; (c) detecting the amount of carbohydrate binding proteins bound to the polysaccharide by the biosensor to obtain glucose concentration of the sample; and (d) refreshing the surface of the biosensor with a washing solution, wherein the washing solution comprises a high concentration glucose solution.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention provides a method for continuously detecting glucose concentration in a sample. The invention utilizes the affinity difference between the carbohydrate binding protein to glucose and that to polysaccharide and combines with a biosensor to detected glucose concentration in a sample. Thus, providing stable and continuous detection of glucose concentrations and solving the problem mentioned above.

Figure 1A:
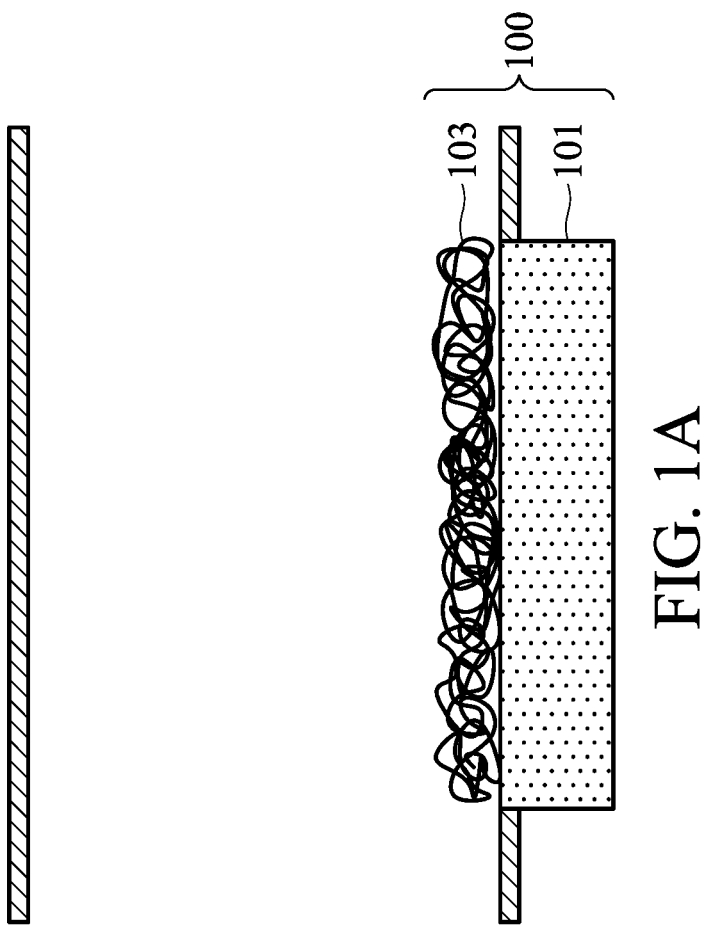
FIGS. 1A-1C show a schematic view of the method for continuously detecting glucose concentration in a sample of the invention.
Figure 1B:
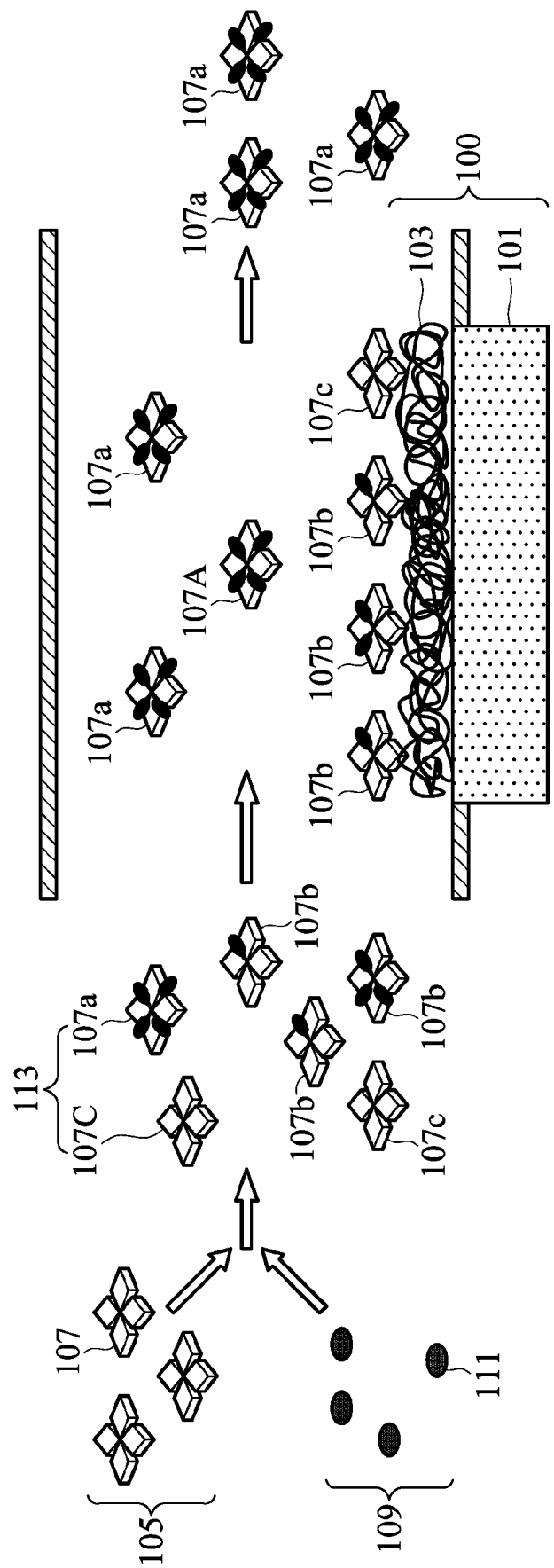
Figure 1C:
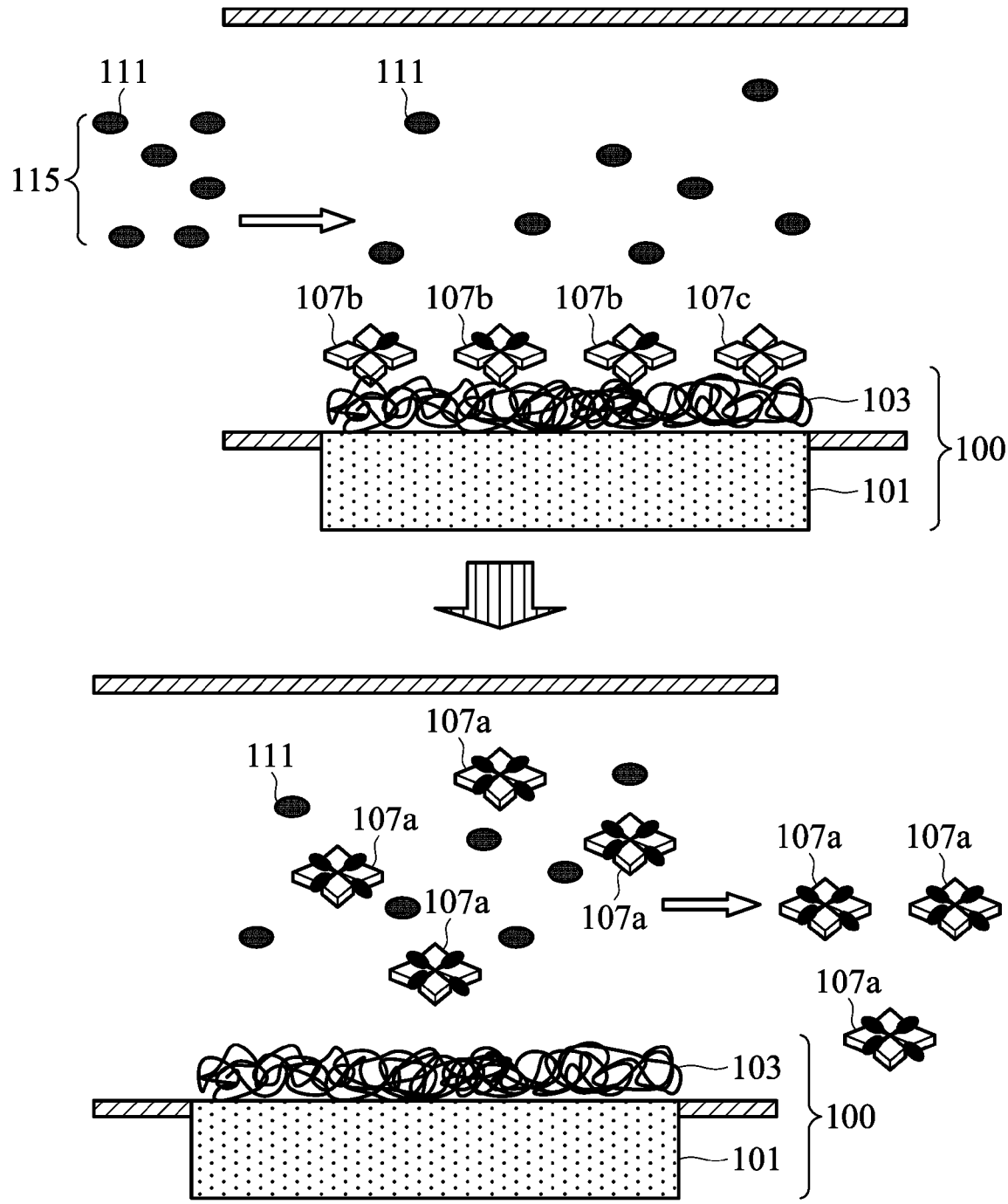

In one aspect of the invention, a method for continuously detecting glucose concentration in a sample is provided as shown in FIGS. 1A-1C. Referring to FIG. 1A, first, a biosensor 100 is provided, wherein the biosensor 100 may comprise a transducer 101 and a polysaccharide 103 covered on the surface of the transducer 101. The polysaccharide may be through a process of physical adsorption, or self assembling, or coating, or covalent binding to be covered on the surface of the transducer. The transducer 101 may comprise a mass sensitive element, an optical element, an electrical element, an electrochemical element or an acoustic element. In one embodiment, the transducer 101 may comprise a quartz crystal microbalance (QCM) or a surface plasmon resonance transducer (SPR transducer) or a surface acoustic wave element (SAW element). The polysaccharide 103 may comprise a dextran or a dextrin.

Referring to FIG. 1B, then, a carbohydrate binding protein solution with a particular concentration 105 is provided, wherein the carbohydrate binding protein 107 has at least one receptor, and the receptor is capable of binding to the polysaccharide and glucose. The particular concentration of the carbohydrate binding protein solution may be adjusted according to the condition of the detection. In one embodiment, the concentration of the carbohydrate binding protein solution is about 0.12-0.24%. In addition, the affinity of the receptor of the carbohydrate binding protein 107 to glucose is greater than that to the polysaccharide. The carbohydrate binding protein 107 may comprise a lectin, such as a concanavaline A (Con A), a wheat germ agglutintin (WGA), a peanut agglutinin (PNA) or a soybean agglutinin (SBA).

Next, a sample 109 and the carbohydrate binding protein solution with a particular concentration 105 are mixed to form a mixture 113. When mixed, glucose 111 in the sample binds to the receptors of the carbohydrate binding protein 107 so that the mixture 113 has carbohydrate binding proteins with receptors that are completely occupied by glucose 107a, carbohydrate binding proteins with receptors that are partially occupied by glucose 107b and carbohydrate binding proteins with receptors that are not occupied by glucose 107c.

Afterward, the mixture 113 is contacted with the biosensor 100, and the carbohydrate binding protein with receptors that are partially occupied by glucose 107b and the carbohydrate binding protein with receptors that are not occupied by glucose 107c in the mixture 113 binds to the polysaccharide 103 of the biosensor 100. In a preferred embodiment, a flow detection model may be used for continuous glucose determination and the step of contacting mixture 113 with the biosensor 100 may be performed in a flow channel of the flow detection model. Furthermore, the carbohydrate binding protein with receptors that are partially occupied by glucose 107b and the carbohydrate binding protein with receptors that are not occupied by glucose 107c binding to the polysaccharide 103 of the biosensor 100 generate a physical response or a chemical response. In one embodiment, the physical response or chemical response may comprise a mass change, a viscosity change or a density change. Moreover, the carbohydrate binding protein 107 may further comprise a conjugate used as a source of the physical response or chemical response or a sensitizer for enhancing the physical response or chemical response. The conjugate may comprise a detectable substance, such as a fluorescent dye, an enzyme, an electrical active substance or a nano-particle, etc.

Thereafter, an amount of carbohydrate binding proteins bound to the polysaccharide 103 is detected by the biosensor 100 to obtain glucose concentration of the sample, wherein the glucose concentration of the sample is inversely proportional to the amount of carbohydrate binding proteins bound to the polysaccharide 103 of the biosensor 100. In one embodiment, the biosensor 100 utilizes a transducer 101 to determine the physical response or chemical response generated form the carbohydrate binding protein with receptors that are partially occupied by glucose 107b and the carbohydrate binding protein with receptors that are not occupied by glucose 107c binding to the polysaccharide 103 of the biosensor 100 to detect the amount of carbohydrate binding proteins bound to the polysaccharide.

Referring to FIG. 1C, finally, a high concentration glucose solution 115 is used to wash a surface of the biosensor 100. The affinity of the receptor of the carbohydrate binding protein 107 to glucose is greater than that to polysaccharide. Thus, by using a high concentration glucose solution, when washing the surface of the biosensor 100, the carbohydrate binding protein 107 will switch binding from polysaccharide to glucose. Therefore, the high concentration glucose solution refreshes the surface of the biosensor 100 so that the biosensor can be continuously reused, to continuously detect the glucose concentration in the sample by repeating the steps mentioned above. A concentration of the high concentration glucose solution 115 may be greater than 200 mg/dl and in one embodiment, may be 400-2000 mg/dl.

In addition, the invention also provides a kit which may be used for the method for continuously detecting glucose concentration in a sample of the invention. The kit may comprise a biosensor 100, a reactive solution and a washing solution. The biosensor 100 may comprise a transducer 101 and a polysaccharide 103 covered on the surface of the transducer 101. The transducer 101 may comprise a mass sensitive element, an optical element, an electrical element, an electrochemical element or an acoustic element. In one embodiment, the transducer 101 may comprise a quartz crystal microbalance (QCM) or a surface plasmon resonance transducer (SPR transducer) or a surface acoustic wave element (SAW element). The polysaccharide 103 may comprise a dextran or a dextrin.

The reactive solution is used to react with a sample, which may comprise the carbohydrate binding protein solution with a particular concentration 105, wherein a carbohydrate binding protein 107 has at least one receptor, and the receptor is capable of binding to the polysaccharide and glucose. The particular concentration of the carbohydrate binding protein solution may be adjusted according to the condition of the detection. In one embodiment, the particular concentration of the carbohydrate binding protein solution is about 0.12-0.24%. In addition, the affinity of the receptor of the carbohydrate binding protein 107 to glucose is greater than that to polysaccharide. The carbohydrate binding protein 107 may comprise a lectin, such as a concanavaline A (Con A), a wheat germ agglutintin (WGA), a peanut agglutinin (PNA) or a soybean agglutinin (SBA).

The wash solution is used to refresh the surface of the biosensor, which may comprise the high concentration glucose solution 115. The affinity of the receptor of the carbohydrate binding protein 107 to glucose is greater than that to polysaccharide. Thus, by using a high concentration glucose solution, when washing the surface of the biosensor 100, the carbohydrate binding protein 107 will switch binding from polysaccharide to glucose. Therefore, the high concentration glucose solution refreshes the surface of the biosensor 100 so that the biosensor can be continuously reused, to continuously detect the glucose concentration in the sample by repeating the steps mentioned above. A concentration of the high concentration glucose solution 115 may be greater than 200 mg/dl and in one embodiment, may be 400-2000 mg/dl.

Furthermore, by combining the use of the kit of the invention and the method for continuously detecting glucose concentration in a sample of the invention, a system for continuously detecting glucose concentration in a sample may be obtained.

Moreover, the invention also may be a method for using a biosensor. Refer to FIGS. 1A-1C again. In FIG. 1A, first, a biosensor 100 is provided and the biosensor 100 may comprise a transducer 101 and a polysaccharide 103 covered on the surface of the transducer 101. The transducer 101 may comprise a mass sensitive element, an optical element, an electrical element, an electrochemical element or an acoustic element. In one embodiment, the transducer 101 may comprise a quartz crystal microbalance (QCM) or a surface plasmon resonance transducer (SPR transducer) or a surface acoustic wave element (SAW element). The polysaccharide 103 may comprise a dextran or a dextrin.

Then, in FIG. 1B, a mixture 113 of a reactive solution comprising a carbohydrate binding protein solution with a particular concentration 105 and a sample 109 is contacted with biosensor 100. The carbohydrate 107 is capable of binding to polysaccharide and glucose. The particular concentration of the carbohydrate binding protein solution may be adjusted according to the condition of the detection. In one embodiment, the particular concentration of the carbohydrate binding protein solution is about 0.12-0.24%. In the mixture 113, glucose in the sample binds to the carbohydrate binding protein. The affinity of the receptor of the carbohydrate binding protein 107 to glucose is greater than that to the polysaccharide. The carbohydrate binding protein 107 may comprise a lectin, such as a concanavaline A (Con A), a wheat germ agglutintin (WGA), a peanut agglutinin (PNA) or a soybean agglutinin (SBA).

After the mixture 113 is contacted with biosensor 100, the carbohydrate binding protein with receptors that are partially occupied by glucose 107b and the carbohydrate binding protein with receptors that are not occupied by glucose 107c in the mixture 113 binds to the polysaccharide 103 of the biosensor 100. The carbohydrate binding protein with receptors that are partially occupied by glucose 107b and the carbohydrate binding protein with receptors that are not occupied by glucose 107c binding to the polysaccharide 103 of the biosensor 100 generate a physical response or a chemical response. In one embodiment, the physical response or chemical response may comprise a mass change, a viscosity change or a density change. The carbohydrate binding protein 107 may further comprise a conjugate used as a source of the physical response or chemical response or a sensitizer for enhancing the physical response or chemical response. The conjugate may comprise a detectable substance, such as a fluorescent dye, an enzyme, an electrical active substance or a nano-particle, etc.

Thereafter, an amount of carbohydrate binding proteins bound to the polysaccharide 103 is detected by the biosensor 100 to obtain glucose concentration of the sample. In one embodiment, the biosensor 100 utilizes a transducer 101 to determine the physical response or chemical response generated form the carbohydrate binding protein with receptors partially that are occupied by glucose 107b and the carbohydrate binding protein with receptors that are not occupied by glucose 107c binding to the polysaccharide 103 of the biosensor 100 to detect the amount of carbohydrate binding proteins bound to the polysaccharide.

Finally, referring to FIG. 1C, a surface of the biosensor 100 is refreshed with a washing solution, wherein the washing solution comprises a high concentration glucose solution 115. The affinity of the receptor of the carbohydrate binding protein 107 to glucose is greater than that to polysaccharide. Thus, by using a high concentration glucose solution, when washing the surface of the biosensor 100, the carbohydrate binding protein 107 will switch binding from polysaccharide to glucose. Therefore, the high concentration glucose solution refreshes the surface of the biosensor 100 so that the biosensor can be continuously reused, to continuously detect the glucose concentration in the sample by repeating the steps mentioned above. A concentration of the high concentration glucose solution 115 may be greater than 200 mg/dl and in one embodiment, may be 400-2000 mg/dl.

EXAMPLE

Figure 2:
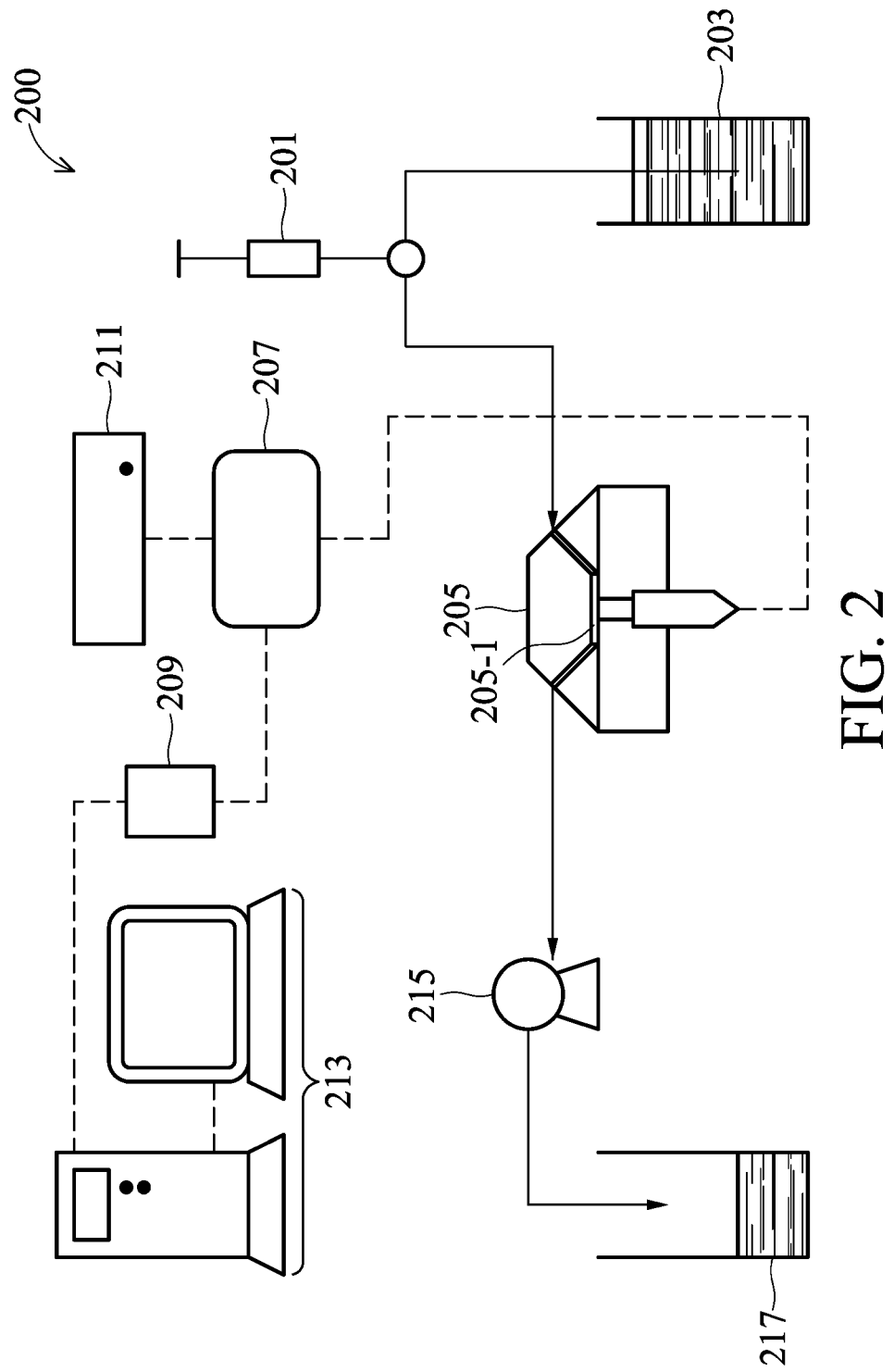
FIG. 2 shows a schematic view of a flow device used in a example of the invention.

A dextran modified (covered) quartz crystal microbalance was used as a biosensor, and combined with a flow detection module 200 (as shown in FIG. 2), and, mixtures of 0.12-0.24% of Con A and glucose solutions with different concentrations were used to determine the glucose concentrations by the method of the invention. The flow detection module 200 comprised an injected sample 201, a mobile phase 203, a flow cell 205, an oscillating circuit 207, a frequency counter 209, a power supply 211, a computer 213, a pump 215 and waste solution 217. The mobile phase provided a liquid phase, usually a buffer solution for the flow channel and flow cell and to move the injected sample 201 to the biosensor 205-1 placed in the flow cell 205 for reaction. The switching between the injected sample 201 and the mobile phase 203 was controlled by a switch to prevent bubbles from forming in the flow channel. A pump was used to control the flow of the liquid in the flow channel. For signal measurement, a quartz crystal microbalance 205-1 was connected to the oscillating circuit to 207 result in resonance at a particular frequency (in this case, the fundamental frequency of QCM was 10 MHz), then the frequency counter 209 could acquire and record the change of an oscillating frequency of the quartz crystal microbalance 205-1. According to the mass-loading effect of the quartz crystal microbalance, the change of an oscillating frequency was caused by physical or chemical response that occurred due to the binding of a carbohydrate binding protein and the polysaccharide was recorded by the frequency counter 209, immediately. Finally, the signal from frequency counter 209 was displayed and continuously monitored by computer 213.

Modifying (Coving) the Transducer with Polysaccharide

The method for modifying the transducer with dextran was as follows:

(1) First, the QCM was treated with 0.5 mM, 16-mercaptohexadecanoic acid (a carboxyl-terminated alkane thiol compound) to form a self-assembling layer having carboxyl groups on a gold electrode of the quartz crystal microbalance.

(2) Activating the carboxyl groups on a surface by 50 mM EDC/200 mM NHS, after activating, 2%, 2-(2-aminoethoxy) ethanol (a amine organic compound with an alcoholic-group) was added to react with NHS ester the surface of the quartz crystal microbalance so that the surface of the quartz crystal microbalance contained the alcoholic-groups.

(3) Epicholorohydrin (0.6 M) was added to react with the alcoholic-group on the surface of the quartz crystal microbalance so that the surface of the quartz crystal microbalance contained the epoxy group.

(4) Finally, 5% dextran (400 KD-40 MD) was added to react with the epoxy group on the surface of the quartz crystal microbalance by covalent binding, then the dextran layer could formed on the surface of the quartz crystal microbalance.

Method for Continuous Detection

First, 0.24% Con A was mixed with glucose sample and injected into the flow channel, then injected sample would flow through the dextran modified quartz crystal microbalance in the flow cell 205 by the mobile phase. At that time, the competition between Con A, glucose, and dextran would occurred, and result in the change of the oscillating frequency of the quartz crystal microbalance. Finally, the frequency change was determined by the frequency counter to correspond to the glucose concentration of the sample. The frequency response was inversely proportional to the concentration of glucose in the sample. After the reaction process was finished, a high concentration glucose solution (1200 mg/dl) was injected into the flow channel to remove Con A attached on the surface of biosensor. Hence, the process of measuring could be repeated (see FIGS. 1A-1C).

Measurement of the Con A-Dextran Complex

Figure 3:
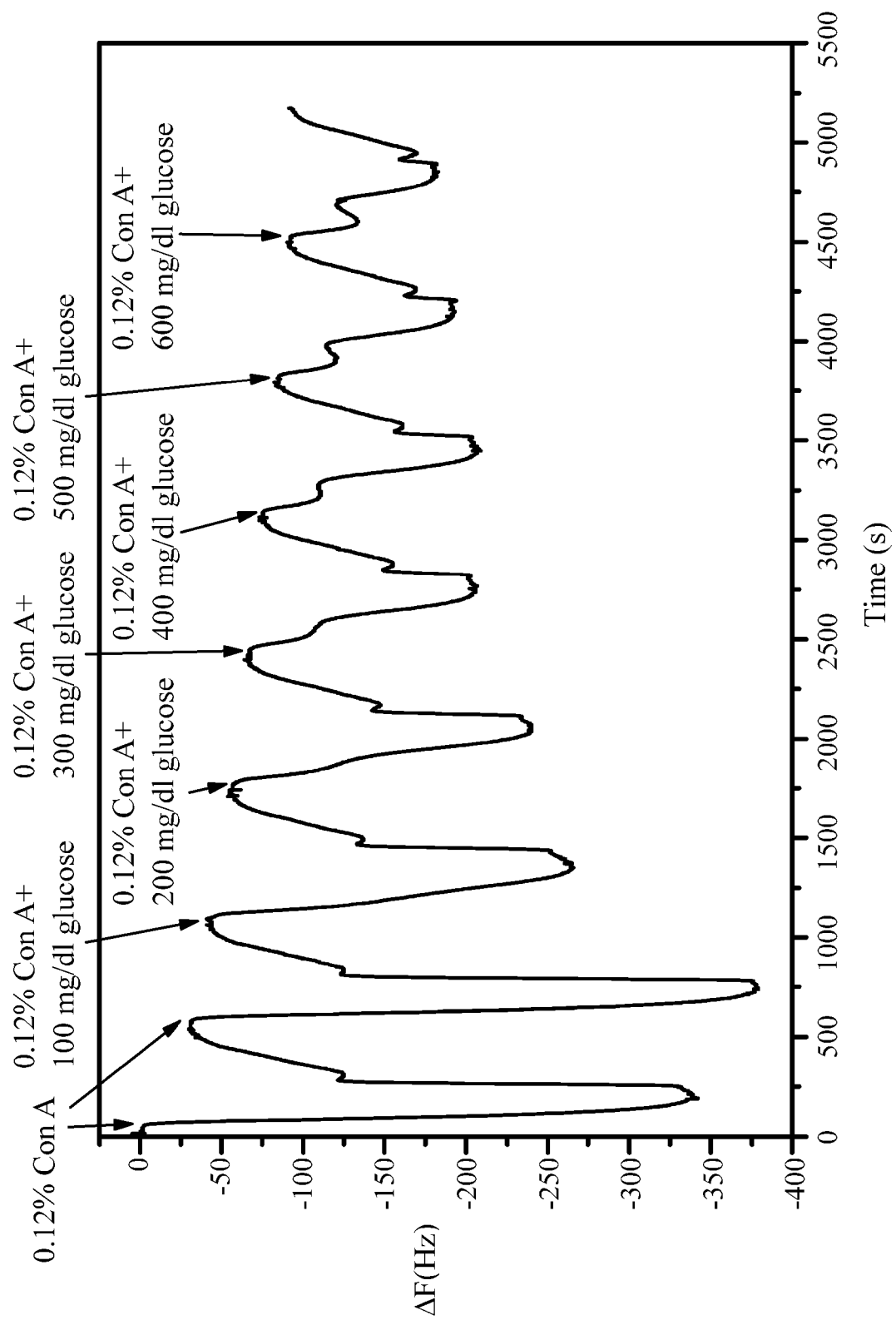
FIG. 3 shows continuous response of the biosensor for the determination of glucose with different concentration.

FIG. 3 shows the response for the continuous measurement of glucose with different concentration. After Con A or Con A-glucose complex was added, the decreasing frequency response was exhibited due to the binding of Con A to dextran on the surface of transducer. Then, after the high concentration glucose solution (1200 mg/dl) was added, because the affinity of the Con A to glucose is greater than that of Con A to the dextran, the recovered signal could be observed. At this time, the Con A attached on the biosensor was removed from the surface. In FIG. 3, the two peaks starting from the left portion of FIG. 3 were the frequency measurement of 0.12% pure Con A and the following six peaks were the frequency measurement of 200, 400, 600, 800, 1000 and 1200 mg/dl of glucose mixed with equal volumes of 0.24% Con A, respectively (note that following mixture, the final concentrations of glucose were 100, 200, 300, 400, 500 and 600 mg/dl and the final concentrations of Con A were 0.12%, respectively). In FIG. 3, the decreased peak region was the increasing weight change due to the binding of the Con A and the dextran on the quartz crystal microbalance and the increasing peak region was the change of the decreasing weight change due to the disassociation of the Con A from the Con A-dextran complex on the quartz crystal microbalance.

Calibration Curve

Figure 4:
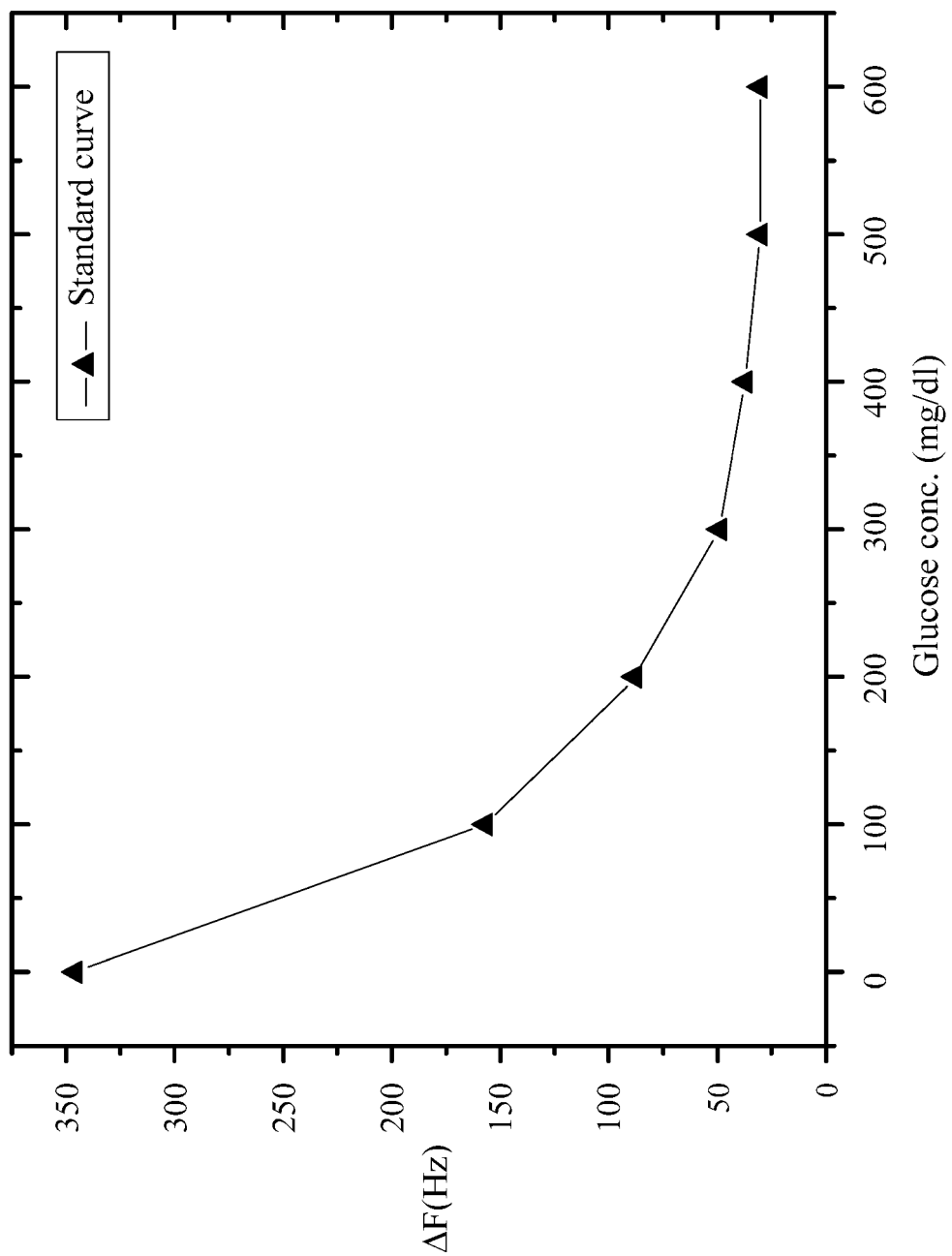
FIG. 4 shows a calibration plot of glucose concentrations versus frequency change thereof.

FIG. 4 shows a calibration plot of glucose concentrations versus frequency change thereof. With glucose concentration in the sample increasing, the signal change gradually decreased.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for continuously detecting glucose concentration in a sample, comprising:
   (a) providing a biosensor comprising a transducer and a polysaccharide covered on a surface of the transducer;
   (b) providing a carbohydrate binding protein solution, wherein the carbohydrate binding protein has at least one receptor, and the receptor is capable of binding to the polysaccharide and glucose;
   (c) mixing a sample and the carbohydrate binding protein solution to form a mixture;
   (d) contacting the mixture with the biosensor;
   (e) detecting the amount of carbohydrate binding proteins bound to the polysaccharide by the biosensor, wherein glucose concentration of the sample is inversely proportional to the amount of carbohydrate binding proteins bound to the polysaccharide;
   (f) refreshing the surface of the transducer with a high concentration glucose solution; and
   (g) repeating the steps (b)-(f) after the step (f).

2. The method for continuously detecting glucose concentration in a sample as claimed in claim 1, wherein the polysaccharide is covered on the surface of the transducer through a process of physical adsorption, or self assembling, or coating, or covalent binding.

3. The method for continuously detecting glucose concentration in a sample as claimed in claim 1, wherein in the step (c), carbohydrate binding proteins with receptors that are partially occupied by glucose or carbohydrate binding proteins with receptors that are not occupied by glucose in the mixture binds to the polysaccharide generating a physical response or a chemical response.

4. The method for continuously detecting glucose concentration in a sample as claimed in claim 3, wherein the physical response or chemical response is determined by the transducer to detect the amount of carbohydrate binding proteins bound to the polysaccharide.

5. The method for continuously detecting glucose concentration in a sample as claimed in claim 3, wherein the physical response or chemical response is a mass change, a viscosity change or a density change.

6. The method for continuously detecting glucose concentration in a sample as claimed in claim 3, wherein the carbohydrate binding protein comprises a conjugate used as a signal source of the physical response or chemical response, or a sensitizer for enhancing the physical response or chemical response.

7. The method for continuously detecting glucose concentration in a sample as claimed in claim 1, wherein the transducer comprises a mass sensitive element, an optical element, an electrical element, an electrochemical element or an acoustic element.

8. The method for continuously detecting glucose concentration in a sample as claimed in claim 1, wherein the transducer comprises a quartz crystal microbalance (QCM) or a surface plasmon resonance transducer (SPR transducer) or a surface acoustic wave element (SAW element).

9. The method for continuously detecting glucose concentration in a sample as claimed in claim 1, wherein the polysaccharide comprises a dextran or a dextrin.

10. The method for continuously detecting glucose concentration in a sample as claimed in claim 1, wherein the carbohydrate binding protein comprises a lectin.

11. The method for continuously detecting glucose concentration in a sample as claimed in claim 1, wherein the carbohydrate binding protein comprises a concanavaline A (Con A), a wheat germ agglutintin (WGA), a peanut agglutinin (PNA) or a soybean agglutinin (SBA).

12. The method for continuously detecting glucose concentration in a sample as claimed in claim 1, wherein a concentration of the high concentration glucose solution is about 400-2000 mg/dl.

13. A kit for continuously detecting glucose concentration in a sample, comprising:
    a biosensor comprising a transducer and a polysaccharide covered on a surface of the transducer;
    a reactive solution for reacting with the sample, wherein the reactive solution comprises a carbohydrate binding protein solution with a particular concentration; and
    a washing solution for refreshing the surface of the transducer, wherein the washing solution comprises a high concentration glucose solution.

14. The kit for continuously detecting glucose concentration in a sample as claimed in claim 13, wherein the transducer comprises a mass sensitive element, an optical element, an electrical element, an electrochemical element or an acoustic element.

15. The kit for continuously detecting glucose concentration in a sample as claimed in claim 13, wherein the transducer comprises a quartz crystal microbalance (QCM) or a surface plasmon resonance transducer (SPR transducer) or a surface acoustic wave element (SAW element).

16. The kit for continuously detecting glucose concentration in a sample as claimed in claim 13, wherein the polysaccharide comprises a dextran or a dextrin.

17. The kit for continuously detecting glucose concentration in a sample as claimed in claim 13, wherein the carbohydrate binding protein comprises a lectin.

18. The kit for continuously detecting glucose concentration in a sample as claimed in claim 13, wherein the carbohydrate binding protein comprises a concanavaline A (Con A), a wheat germ agglutintin (WGA), a peanut agglutinin (PNA) or a soybean agglutinin (SBA).

19. The kit for continuously detecting glucose concentration in a sample as claimed in claim 13, wherein a concentration of the high concentration glucose solution is about 400-2000 mg/dl.

20. A method for using a biosensor, comprising:
(a) providing a biosensor comprising a transducer and a polysaccharide covered on a surface of the transducer;
(b) contacting a mixture of a reactive solution comprising a carbohydrate binding protein solution with a particular concentration and a sample with the biosensor, wherein the carbohydrate binding protein is capable of binding to the polysaccharide and glucose;
(c) detecting the amount of carbohydrate binding proteins bound to the polysaccharide by the biosensor to obtain glucose concentration of the sample; and
(d) refreshing the surface of the transducer with a washing solution, wherein the washing solution comprises a high concentration glucose solution.

21. The method for using a biosensor as claimed in claim 20, wherein the polysaccharide is covered on the surface of the transducer through a process of physical adsorption, or self assembling, or coating, or covalent binding.

22. The method for using a biosensor as claimed in claim 20, further (e) repeating the steps (b)-(d) after the step (d).

23. The method for using a biosensor as claimed in claim 20, wherein in the step (b), a carbohydrate binding protein with receptors that are partially occupied by glucose or a carbohydrate binding protein with receptors that are not occupied by glucose in the mixture binds to the polysaccharide generating a physical response or chemical response.

24. The method for using a biosensor as claimed in claim 23, wherein the physical response or chemical response is determined by the transducer to detect the amount of carbohydrate binding proteins bound to the polysaccharide.

25. The method for using a biosensor as claimed in claim 23, wherein the carbohydrate binding protein comprises a conjugate used as a source of the physical response or chemical response, or a sensitizer for enhancing the physical response or chemical response.

26. The method for using a biosensor as claimed in claim 20, wherein the transducer comprises a mass sensitive element, an optical element, an electrical element, an electrochemical element or an acoustic element.

27. The method for using a biosensor as claimed in claim 20, wherein the transducer comprises a quartz crystal microbalance (QCM) or a surface plasmon resonance transducer (SPR transducer) or a surface acoustic wave element (SAW element).

28. The method for using a biosensor as claimed in claim 20, wherein the polysaccharide comprises a dextran or a dextrin.

29. The method for using a biosensor as claimed in claim 20, wherein the carbohydrate binding protein comprises a lectin.

30. The method for using a biosensor as claimed in claim 20, wherein the carbohydrate binding protein comprises a concanavaline A (Con A), a wheat germ agglutintin (WGA), a peanut agglutinin (PNA) or a soybean agglutinin (SBA).

31. The method for using a biosensor as claimed in claim 20, wherein a concentration of the high concentration glucose solution is about 400-2000 mg/dl.

* * * * *